(12) United States Patent
Saka et al.

(10) Patent No.: US 6,747,161 B2
(45) Date of Patent: Jun. 8, 2004

(54) PROCESS FOR CYCLIZING OPTICALLY ACTIVE 4-AMINO-2-HALOGENOBUTYRIC ACIDS

(75) Inventors: Yasuhiro Saka, Akashi (JP); Tatsuya Honda, Kobe (JP); Nobuo Nagashima, Takasago (JP)

(73) Assignee: Kaneka Corporation, Osaka (JP)

( * ) Notice: Subject to any disclaimer, the term of this patent is extended or adjusted under 35 U.S.C. 154(b) by 120 days.

(21) Appl. No.: 10/182,649

(22) PCT Filed: Feb. 2, 2001

(86) PCT No.: PCT/JP01/00736

§ 371 (c)(1),
(2), (4) Date: Nov. 1, 2002

(87) PCT Pub. No.: WO01/56985

PCT Pub. Date: Aug. 9, 2001

(65) Prior Publication Data

US 2003/0109719 A1 Jun. 12, 2003

(30) Foreign Application Priority Data

Feb. 4, 2000 (JP) ........................................ 2000-027909

(51) Int. Cl.[7] ............................................. C07D 205/00
(52) U.S. Cl. ................................................... 548/953
(58) Field of Search ......................................... 548/953

(56) References Cited

U.S. PATENT DOCUMENTS 6,333,418 B1 * 12/2001 Parratt et al. ............... 548/953

FOREIGN PATENT DOCUMENTS

| EP | 1170287 A1 | 1/2002 |
| JP | 10-120648 | 5/1998 |
| WO | WO 00/03982 A1 | 1/2000 |
| WO | WO 00/69817 A1 | 11/2000 |
| WO | WO 01/55104 A1 | 8/2001 |

OTHER PUBLICATIONS

"The Syntheseis of ±–Azetidine–2–carboxylic Acid and 2–Pyrrolidinone Derivatives", XP009004623, Agr. Biol. Chem., 37(3), 649–652, 1973.
Chemical Abstracts, vol. 51, pp. 3547g–3548I & Biochem. J., (1956), 64, pp. 323–332.

* cited by examiner

*Primary Examiner*—Joseph K. McKane
*Assistant Examiner*—Robert Shiao
(74) *Attorney, Agent, or Firm*—Sughrue Mion, PLLC

(57) ABSTRACT

The invention provides a process for producing optically active azetidine-2-carboxylic acid with good efficiency, expedience, and commercial advantage, which comprises cyclizing an optically active 4-amino-2-halogenobutyric acid in an optical yield of as high as 90% or more.

It is a process for producing optically active azetidine-2-carboxylic acid of the general formula (2), in which * denotes an asymmetric carbon atom, which comprises cyclizing an optically active 4-amino-2-halogenobutyric acid of the general formula (1), in which X represents a halogen atom and * denotes an asymmetric carbon atom, in the presence of an oxide of an alkaline earth metal, a hydroxide of an alkaline earth metal excepting barium, or an organic amine.

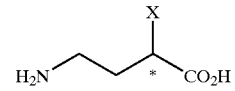

(1)

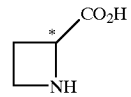

(2)

20 Claims, No Drawings

PROCESS FOR CYCLIZING OPTICALLY ACTIVE 4-AMINO-2-HALOGENOBUTYRIC ACIDS

This is a National stage entry under 35 U.S.C. § 371 of PCT/JP01/00736 filed Feb. 2, 2001, the disclosure of which is incorporated herein by reference.

TECHNICAL FIELD

The present invention relates to a process for producing an optically active azetidine-2-carboxylic acid, which is of value as a production intermediate of pharmaceuticals or the like, through the cyclization of an optically active 4-amino-2-halogenobutyric acid.

BACKGROUND ART

The following processes are known for the production of azetidine-2-carboxylic acid through utilization of the cyclization reaction of a 4-amino-2-halogenobutyric acid.

(1) A process which comprises subjecting hydrochloric acid-nitrous acid to act on (S)-2,4-diaminobutyric acid to give (S)-4-amino-2-chlorobutyric acid and, then, heating it in an aqueous solution of barium hydroxide to give (R)-azetidine-2-carboxylic acid (Biochemical Journal, 64, 323 (1956)).

(2) A process which comprises subjecting dimethyl sulfate to act on pyrrolidin-2-one to give methoxyimine, brominating it with N-bromosuccinimide, hydrolyzing the same to DL-4-amino-2-bromobutyric acid, and heat-treating it in an aqueous solution of barium hydroxide or sodium hydroxide to give DL-azetidine-2-carboxylic acid (Agricultural and Biological Chemistry, 37, 649 (1973).

However, the above processes have the following drawbacks.

In process (1) wherein the cyclization reaction is conducted under heating at a high temperature in an aqueous solution of barium hydroxide, the optically active compound undergoes racemization to drastically reduce the optical purity of the product. Of the product with such a drastically reduced optical purity, one of the enantiomers is generally unwanted and an optical resolution or the like procedure is required for improving the optical purity. Moreover, the unwanted enantiomer so separated has to be discarded unless a profitable racemization method is available, with the result that the process is not economical and does not lend itself well to commercial production.

In process (2), the product azetidine-2-carboxylic acid is a racemic compound and the resolution of this racemic compound is necessary for obtaining the optically active compound. Moreover, after resolution the unwanted enantiomer has to be discarded unless a profitable racemization method is available so that this process is not economical and does not lend itself well to commercial production.

SUMMARY OF THE INVENTION

In view of the above state of the art, the present invention has its object to provide an efficient, economical and commercially profitable process for producing an optically active azetidine-2-carboxylic acid.

The inventors of the present invention did much research for overcoming the above-mentioned disadvantages and have ultimately developed the present invention.

The present invention, therefore, is directed to a process for producing optically active azetidine-2-carboxylic acid of the general formula (2):

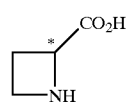

(2)

(wherein * denotes an asymmetric carbon atom) which comprises cyclizing an optically active 4-amino-2-halogenobutyric acid represented by the general formula (1):

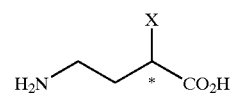

(1)

(wherein X represents a halogen atom; * denotes an asymmetric carbon atom) in the presence of an oxide of an alkaline earth metal, a hydroxide of an alkaline earth metal excepting barium, or an organic amine. In accordance with the present invention, there is provided a process for producing optically active azetidine-2-carboxylic acid in high optical yield.

The present invention is now described in detail.

DISCLOSURE OF INVENTION

The starting material of the invention, namely an optically active 4-amino-2-halogenobutyric acid, may be whichever of the pure (R)-compound and the pure (S)-compound or a mixture of these compounds containing either enantiomer in excess but for the production of optically active azetidine-2-carboxylic acid, the material of high optical purity is, of course, preferred. Moreover, the halogen atom of said optically active 4-amino-2-halogenobutyric acid may be a fluorine, a chlorine, a bromine or an iodine atom but is preferably a chlorine or a bromine atom.

As such an optically active 4-amino-2-halogenobutyric acid, (S)-4-amino-2-chlorobutyric acid, for instance, can be obtained from (S)-2,4-diaminobutyric acid by the process described in Biochemical Journal, 64, 323 (1956). Moreover, by the process described in JPA Hei-11-169620, an (R)-4-amino-2-halogenobutyric acid ester can be hydrolyzed in an aqueous solution of a mineral acid to give a hydrolyzate solution containing an (R)-4-amino-2-halogenobutyric acid. This hydrolyzate solution may be neutralized with an alkali metal base, for instance, and directly submitted to the cyclization reaction or the neutralized solution may further be purified by ion exchange column chromatography to isolate the optically active (R)-4-amino-2-halogenobutyric acid.

The optically active 4-amino-2-halogenobutyric acid of general formula (1), thus obtained, can be cyclized in the presence of a base, such as an oxide of an alkaline earth metal, a hydroxide of an alkaline earth metal excepting barium, or an organic amine to produce optically active azetidine-2-carboxylic acid of general formula (2) in good optical yield.

The oxide of an alkaline earth metal which can be used in the cyclization reaction includes magnesium oxide, calcium oxide, barium oxide, etc., with magnesium oxide being particularly preferred. The hydroxide of an alkaline earth metal includes magnesium hydroxide, calcium hydroxide, etc., although magnesium hydroxide is particularly preferred.

As the organic amine, a secondary amine or a tertiary amine can be used with advantage. Among preferred examples are secondary alkylamines such as dimethylamine, diethylamine, dipropylamine, diisopropylamine, dibutylamine, diisobutylamine, di-sec-butylamine, di-tert-butylamine, dipentylamine, dihexylamine, diheptylamine, dioctylamine, dicyclohexylamine, etc.; secondary cycloalkylamines such as piperidine, piperazine, 2,2,6,6-tetramethylpiperidine, etc.; secondary arylamines such as diphenylamine, ditolylamine, etc.; secondary arylalkylamines such as dibenzylamine etc.; tertiary alkylamines such as trimethylamine, triethylamine, tripropylamine, triisopropylamine, tributylamine, triisobutylamine, diisopropylethylamine, diisobutylmethylamine, N,N-diethyl-tert-octylamine, etc.; tertiary cycloalkylamines such as 4-(dimethylamino)-1,2,2,6,6-pentamethylpiperidine etc.; tertiary arylamines such as triphenylamine, tritolylamine, etc.; tertiary arylalkylamines such as tribenzylamine etc.; polycyclic tertiary cycloamines such as 1,8-diazabicyclo[4.5.0]undecene, 1,5-diazabicyclo[4.3.0]nonene, 1,4-diazabicyclo[2.2.2]octane, etc.; and tertiary aminealcohols such as N,N-dimethylethanolamine, N,N-diethylethanolamine, N,N-dipropylethanolamine, etc., although diisopropylamine, 2,2,6,6-tetramethylpiperidine, triethylamine, diisopropylethylamine, 1,8-diazabicyclo[4.5.0]undecene, and N,N-dimethylethanolamine are particularly preferred.

The level of use of said base is not particularly restricted but the cyclization reaction can be carried out generally in the presence of 1 to 30 molar equivalents of the base relative to the optically active 4-amino-2-halogenobutyric acid (1). The generally preferred level is 1 to 10 molar equivalents.

For the above cyclization reaction, a solvent is generally employed. This solvent is preferably water or a mixture of water and a water-soluble organic solvent which is freely miscible with water. The water-soluble organic solvent mentioned just above includes methanol, ethanol, isopropyl alcohol, tert-butyl alcohol, acetone, acetonitrile, N,N-dimethylformamide and N,N-dimethylacetamide, to mention just a few examples. The organic solvent can be used in a proportion of 1 to 100 volume %, preferably 1 to 50 volume %, relative to water.

The concentration of the optically active 4-amino-2-halogenobutyric acid (1) in the cyclization reaction system is generally 0.5 to 50 weight %, preferably 1 to 30 weight %.

The cyclization reaction temperature varies with different types of base used but is usually within the range of the freezing point to the boiling point of the reaction solvent, namely water or mixture of water and a water-soluble organic solvent. To allow the reaction to go to completion in a short time, the reaction is preferably conducted at a high temperature, but for preventing racemization during the reaction, the reaction temperature is preferably low. Generally speaking, the reaction temperature is 30 to 100° C., more preferably 50 to 100° C.

The cyclization reaction time depends on the type and equivalent of said base and the reaction temperature, but assuming that the reaction temperature is 80 to 100° C., for instance, the reaction can be usually carried to completion in about 20 minutes to about 12 hours.

While the cyclization reaction can be conducted under the above conditions, this cyclization reaction is a substitution cyclization reaction involving a stereochemical inversion of the halogen substituent in the 2-position of the optically active 4-amino-2-halogenobutyric acid (1) and gives rise to the (R)-form of azetidine-2-carboxylic acid from the (S)-form of the staring compound or the (S) form of azetidine-2-carboxylic acid from the (R)-form of the starting compound. Moreover, by adjusting the reaction conditions judiciously, the optical yield of this cyclization reaction can be increased to as high as 90% or more. The term "optical yield" as used herein means the percentage of the optical purity (enantiomeric excess, % ee) of the reaction product optically active azetidine-2-carboxylic acid relative to the optical purity (enantiomeric excess, % ee) of the starting material optically active 4-amino-2-halogenobutyric acid.

Referring to the isolation of the reaction product after completion of the above cyclization reaction, taking the case in which an inorganic base is used as an example, the objective optically active azetidine-2-carboxylic acid can be isolated by neutralizing the base with an acid in the first place and purifying the reaction mixture by ion exchange column chromatography. In the case where an organic amine is used, the optically active azetidine-2-carboxylic acid can be isolated by subjecting the reaction mixture to phase separation to remove the residual organic amine as an organic layer and then purifying the aqueous layer by ion exchange column chromatography. Furthermore, where necessary, the optical purity can be increased by crystallization.

Moreover, the cyclization reaction mixture may be directly subjected to an amino-protecting reaction bypassing isolation of the cyclization product and the resulting amino-protected optically active azetidine-2-carboxylic acid derivative be isolated by the routine procedure such as extraction, concentration, chromatography, and/or crystallization.

BEST MODE FOR CARRYING OUT THE INVENTION

The following examples illustrate the present invention in further detail without defining the scope of the invention.

EXAMPLE 1

To 27.6 ml of an aqueous solution containing 350.8 mg of (R)-4-amino-2-chlorobutyric acid (optical purity 78.4% ee) was added 157.2 mg of magnesium oxide, and the reaction was carried out at 90° C. for 3 hours. Without isolating the (S)-azetidine-2-carboxylic acid formed in there action mixture, 2.5 ml of di-tert-butyl dicarbonate was added to the reaction mixture and the reaction was further conducted at room temperature overnight. This reaction mixture was adjusted to pH 2.0 with 6N-hydrochloric acid and extracted with 3 portions of ethyl acetate. The organic layer was washed with a saturated aqueous solution of sodium chloride and dried over anhydrous sodium sulfate, and the solvent was distilled off to obtain (S)-N-(tert-butoxycarbonyl)azetidine-2-carboxylic acid (yield 60.2%, optical purity 76.3% ee, optical yield 97.3%).

$^1$H-NMR (CDCl$_3$) δ 1.48 (s, 9H), 2.40–2.60 (bs, 2H), 3.80–4.00 (bs, 2H), 4.80 (t, 1H)

$^{13}$C-NMR (CDCl$_3$) δ 19.9, 28.3, 47.2, 60.4, 81.6, 157.3, 173.5

The yield was determined by high performance liquid chromatography using a high-purity product of (S)-N-(tert-butoxycarbonyl)azetidine-2-carboxylic acid as a standard. The optical purity was determined by high performance liquid chromatography under the following conditions.

HPLC (Condition for Optical Purity Analysis)

Column: Chiral Cell OD-R (Daicel), 4.6 mm in. dia.×25 cm long
Eluent: acetonitrile/perchloric acid aq. sol. (pH 2.0)=1/6
Column flow rate: 0.7 ml/min.
Column temperature: 30° C.
Detection wavelength: UV210 nm
Retention time: (S)-N-(tert-butoxycarbonyl)azetidine-2-carboxylic acid: ca 35 min; (R)-N-(tert-butoxycarbonyl)azetidine-2-carboxylic acid: ca 40 min.

EXAMPLE 2

To 6.85 ml of an aqueous solution containing 365.4 mg of (R)-4-amino-2-chlorobutyric acid (optical purity 94.2% ee) was added 232.8 mg of magnesium hydroxide, and the reaction was conducted at 90° C. for 7 hours. Without isolating the (S)-azetidine-2-carboxylic acid formed in the reaction mixture, 1.13 g of sodium carbonate and 1.2 ml of di-tert-butyl dicarbonate were added to the reaction mixture and the reaction was further carried out at room temperature overnight. This reaction mixture was adjusted to pH 2.0 with 6N-hydrochloric acid and extracted with 3 portions of ethyl acetate. The organic layer was washed with a saturated aqueous solution of sodium chloride and dried over anhydrous sodium sulfate. The solvent was then distilled off to obtain (S)-N-(tert-butoxycarbonyl)azetidine-2-carboxylic acid (yield 34.8%, optical purity 90.0% ee, optical yield 96.8%). The yield and optical purity were determined in the same manner as in Example 1.

EXAMPLE 3

To 27.6 ml of an aqueous solution containing 350.8 mg of (R)-4-amino-2-chlorobutyric acid (optical purity 78.4% ee) was added 1.43 ml of diisopropylamine, and the reaction was carried out at 90° C. for 3 hours. Without isolating the (S)-azetidine-2-carboxylic acid formed in the reaction mixture, 2.5 ml of di-tert-butyl dicarbonate was added to the reaction mixture and the reaction was further conducted at room temperature overnight. This reaction mixture was adjusted to pH 2.0 with 6N-hydrochloric acid and extracted with 3 portions of ethyl acetate. The organic layer was washed with a saturated aqueous solution of sodium chloride and dried over anhydrous sodium sulfate, and the solvent was distilled off to obtain (S)-N-(tert-butoxycarbonyl) azetidine-2-carboxylic acid (yield 55.2%, optical purity 75.7% ee, optical yield 96.5%). The yield and optical purity were determined in the same manner as in Example 1.

EXAMPLE 4

To 30.5 ml of an aqueous solution containing 348.0 mg of (R)-4-amino-2-chlorobutyric acid (optical purity 92.9% ee) was added 1.77 ml of 2,2,6,6-tetramethylpiperidine, and the reaction was carried out at 90° C. for 2.75 hours. Without isolating the (S)-azetidine-2-carboxylic acid formed in the reaction mixture, 2.6 ml of di-tert-butyl dicarbonate was added to the reaction mixture and the reaction was further conducted at room temperature overnight. This reaction mixture was adjusted to pH 2.0 with 6N-hydrochloric acid and extracted with 3 portions of ethyl acetate. The organic layer was washed with a saturated aqueous solution of sodium chloride and dried over anhydrous sodium sulfate, and the solvent was distilled off to obtain (S)-N-(tert-butoxycarbonyl)azetidine-2-carboxylic acid (yield 57.3%, optical purity 88.6% ee, optical yield 95.3%). The yield and optical purity were determined in the same manner as in Example 1.

EXAMPLE 5

To 30.8 ml of an aqueous solution containing 361.8 mg of (R)-4-amino-2-chlorobutyric acid (optical purity 92.9% ee) was added 1.83 ml of diisopropylethylamine, and the reaction was carried out at 90° C. for 4 hours. Without isolating the (S)-azetidine-2-carboxylic acid formed in the reaction mixture, 1.3 ml of di-tert-butyl dicarbonate was added to the reaction mixture and the reaction was further conducted at room temperature overnight. This reaction mixture was adjusted to pH 2.0 with 6N-hydrochloric acid and extracted with 3 portions of ethyl acetate. The organic layer was washed with a saturated aqueous solution of sodium chloride and dried over anhydrous sodium sulfate, and the solvent was distilled off to obtain (S)-N-(tert-butoxycarbonyl) azetidine-2-carboxylic acid (yield 48.1%, optical purity 89.0% ee, optical yield 95.8%). The yield and optical purity were determined in the same manner as in Example 1.

EXAMPLE 6

To 30.0 ml of an aqueous solution containing 375.5 mg of (R)-4-amino-2-chlorobutyric acid (optical purity 92.9% ee) was added 1.57 ml of 1,8-diazabicyclo[4.5.0]undecene, and the reaction was carried out at 90° C. for 3.5 hours. Without isolating the (S)-azetidine-2-carboxylic acid formed in the reaction mixture, 1.3 ml of di-tert-butyl dicarbonate was added to the reaction mixture and the reaction was further conducted at room temperature overnight. This reaction mixture was adjusted to pH 2.0 with 6N-hydrochloric acid and extracted with 3 portions of ethyl acetate. The organic layer was washed with a saturated aqueous solution of sodium chloride and dried over anhydrous sodium sulfate, and the solvent was distilled off to obtain (S)-N-(tert-butoxycarbonyl)azetidine-2-carboxylic acid (yield 49.4%, optical purity 87.1% ee, optical yield 93.8%). The yield and optical purity were determined in the same manner as in Example 1.

EXAMPLE 7

To 30.0 ml of an aqueous solution containing 374.1 mg of (R)-4-amino-2-chlorobutyric acid (optical purity 92.9% ee) was added 1.09 ml of N,N-dimethylethanolamine, and the reaction was carried out at 90° C. for 3.5 hours. Without isolating the (S)-azetidine-2-carboxylic acid formed in the reaction mixture, 1.3 ml of di-tert-butyl dicarbonate was added to the reaction mixture and the reaction was further conducted at room temperature overnight. This reaction mixture was adjusted to pH 2.0 with 6N-hydrochloric acid and extracted with 3 portions of ethyl acetate. The organic layer was washed with a saturated aqueous solution of sodium chloride and dried over anhydrous sodium sulfate, and the solvent was distilled off to obtain (S)-N-(tert-butoxycarbonyl)azetidine-2-carboxylic acid (yield 32.3%, optical purity 86.8% ee, optical yield 93.4%). The yield and optical purity were determined in the same manner as in Example 1.

EXAMPLE 8

To 27.6 ml of an aqueous solution containing 350.8 mg of (R)-4-amino-2-chlorobutyric acid (optical purity 78.4% ee) was added 1.50 ml of triethylamine, and the reaction was carried out at 90° C. for 3 hours and 20 minutes. Without isolating the (S)-azetidine-2-carboxylic acid formed in the reaction mixture, 1.3 ml of di-tert-butyl dicarbonate was added to the reaction mixture and the reaction was further conducted at room temperature overnight. This reaction mixture was adjusted to pH 2.0 with 6N-hydrochloric acid and extracted with 3 portions of ethyl acetate. The organic layer was washed with a saturated aqueous solution of sodium chloride and dried over anhydrous sodium sulfate, and the solvent was distilled off to obtain (S)-N-(tert-butoxycarbonyl)azetidine-2-carboxylic acid (yield 51.1%, optical purity 71.2% ee, optical yield 90.8%). The yield and optical purity were determined in the same manner as in Example 1.

COMPARATIVE EXAMPLE 1

To 400 ml of an aqueous solution containing 9.36 g of (R)-4-amino-2-chlorobutyric acid (optical purity 78.4% ee)

was added 43.4 g of barium hydroxide octahydrate, and the reaction was carried out at 90° C. for 2 hours. Without isolating the (S)-azetidine-2-carboxylic acid formed in the reaction mixture, the reaction mixture was adjusted to pH 7.0 with concentrated hydrochloric acid and 50.5 g of sodium carbonate and 31.6 g of di-tert-butyl dicarbonate were serially added to the reaction mixture. The reaction was then carried out at room temperature overnight. This reaction mixture was adjusted to pH 2.0 with 6N-hydrochloric acid and extracted with 3 portions of ethyl acetate. The organic layer was washed with a saturated aqueous solution of sodium chloride and dried over anhydrous sodium sulfate, and the solvent was distilled off to obtain (S)-N-(tert-butoxycarbonyl)azetidine-2-carboxylic acid (yield 52.6%, optical purity 63.7% ee, optical yield 81.3%). The yield and optical purity were determined in the same manner as in Example 1.

COMPARATIVE EXAMPLE 2

To 400 ml of an aqueous solution containing 9.36 g of (R)-4-amino-2-chlorobutyric acid (optical purity 78.4% ee) was added 11 g of sodium hydroxide, and the reaction was carried out at 90° C. for 4 hours. Without isolating the (S)-azetidine-2-carboxylic acid formed in the reaction mixture, the reaction mixture was adjusted to pH 7.0 with concentrated hydrochloric acid and 64.9 g of sodium carbonate and 31.6 g of di-tert-butyl dicarbonate were serially added to the reaction mixture. The reaction was then carried out at room temperature overnight. This reaction mixture was adjusted to pH 2.0 with 6N-hydrochloric acid and extracted with 3 portions of ethyl acetate. The organic layer was washed with a saturated aqueous solution of sodium chloride and dried over anhydrous sodium sulfate, and the solvent was distilled off to obtain (S)-N-(tert-butoxycarbonyl)azetidine-2-carboxylic acid (yield 48.0%, optical purity 56.4% ee, optical yield 71.9%). The yield and optical purity were determined in the same manner as in Example 1.

REFERENCE EXAMPLE 1

Synthesis of (R)-4-amino-2-chlorobutyric Acid

In 1900 ml of 1M aqueous sulfuric acid was dissolved 38 g of methyl (R)-4-amino-2-chlorobutyrate (optical purity 79.1% ee), and the reaction was conducted at room temperature for 72 hours. This reaction mixture was neutralized with 210 g of sodium carbonate, whereby an aqueous solution of (R)-4-amino-2-chlorobutyric acid was obtained in quantitative yield (optical purity 78.4% ee). This reaction mixture was directly subjected to cyclization reaction.

REFERENCE EXAMPLE 2

In 45 ml of 1M aqueous sulfuric acid was dissolved 4.53 g of methyl (R)-4-amino-2-chlorobutyrate (optical purity 94.2% ee), and the reaction was conducted at room temperature for 48 hours as in Reference Example 1. This reaction mixture was neutralized with sodium carbonate to give an aqueous solution of (R)-4-amino-2-chlorobutyric acid in quantitative yield (optical purity 94.2% ee) This reaction mixture was subjected to cyclization reaction, as diluted at each time of use.

INDUSTRIAL APPLICABILITY

In accordance with the production process of the invention, an optically active 4-amino-2-halogenobutyric acid can be cyclized in the presence of an oxide of an alkaline earth metal, a hydroxide of an alkaline earth metal excepting barium, or an organic amine to produce optically active azetidine-2-carboxylic acid in an optical yield of as high as 90% or more with good efficiency, expedience, and commercial advantage.

What is claimed is:

1. A process for producing an optically active azetidine-2-carboxylic acid of the general formula (2):

in the formula, * denotes an asymmetric carbon atom, which comprises cyclizing an optically active 4-amino-2-halogenobutyric acid of the general formula (1):

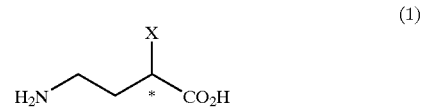

in the formula, X represents a halogen atom and * denotes an asymmetric carbon atom, in the presence of an oxide of an alkaline earth metal, a hydroxide of an alkaline earth metal excepting barium, or an organic amine.

2. The process according to claim 1, wherein the oxide of an alkaline earth metal is magnesium oxide.

3. The process according to claim 1, wherein the hydroxide of an alkaline earth metal is magnesium hydroxide.

4. The process according to claim 1, wherein the organic amine is a secondary amine or a tertiary amine.

5. The process according to claim 4, wherein the secondary amine is 2,2,6,6-tetramethylpiperidine or diisopropylamine and the tertiary amine is diisopropylethylamine, triethylamine, 1,8-diazabicyclo[4.5.0]undecene, or N,N-dimethylethanolamine.

6. The process according to claim 1, wherein the halogen atom is a chlorine or a bromine atom.

7. The process according to claim 1, wherein water or a mixture of water and a water-soluble organic solvent is used as a solvent for cyclization reaction.

8. The process according to claim 1, wherein an optical yield of the cyclization reaction is not less than 90%.

9. The process according to claim 2, wherein the halogen atom is a chlorine or a bromine atom.

10. The process according to claim 3, wherein the halogen atom is a chlorine or a bromine atom.

11. The process according to claim 4, wherein the halogen atom is a chlorine or a bromine atom.

12. The process according to claim 5, wherein the halogen atom is a chlorine or a bromine atom.

13. The process according to claim 2, wherein water or a mixture of water and a water-soluble organic solvent is used as a solvent for cyclization reaction.

14. The process according to claim 3, wherein water or a mixture of water and a water-soluble organic solvent is used as a solvent for cyclization reaction.

15. The process according to claim 4,
wherein water or a mixture of water and a water-soluble organic solvent is used as a solvent for cyclization reaction.

16. The process according to claim 5,
wherein water or a mixture of water and a water-soluble organic solvent is used as a solvent for cyclization reaction.

17. The process according to claim 6,
wherein water or a mixture of water and a water-soluble organic solvent is used as a solvent for cyclization reaction.

18. The process according to claim 2,
wherein an optical yield of the cyclization reaction is not less than 90%.

19. The process according to claim 3,
wherein an optical yield of the cyclization reaction is not less than 90%.

20. The process according to claim 4,
wherein an optical yield of the cyclization reaction is not less than 90%.

* * * * *